United States Patent [19]

Lindstrom

[11] Patent Number: 4,793,357

[45] Date of Patent: Dec. 27, 1988

[54] CT BLOOD FLOW MAPPING WITH XENON GAS ENHANCEMENT

[75] Inventor: Walter W. Lindstrom, Shaker Hts., Ohio

[73] Assignee: Picker International, Inc., Highland Hts., Ohio

[21] Appl. No.: 933,781

[22] Filed: Nov. 24, 1986

[51] Int. Cl.⁴ ............................................. A61B 6/00
[52] U.S. Cl. .................................. 128/654; 128/659; 128/719
[58] Field of Search ............... 128/653, 659, 719, 730, 128/654; 250/303, 380

[56] References Cited

U.S. PATENT DOCUMENTS

| | | | |
|---|---|---|---|
| 3,890,959 | 6/1975 | Youdin et al. | 128/654 |
| 4,334,240 | 6/1982 | Franklin | 358/80 |
| 4,497,024 | 1/1985 | Roth | 128/659 |
| 4,534,223 | 8/1985 | Sinha et al. | 73/708 |
| 4,535,780 | 8/1985 | Gur et al. | 128/569 |
| 4,610,258 | 9/1986 | Colsher | 128/691 |
| 4,622,976 | 11/1986 | Timpe et al. | 128/654 |
| 4,658,827 | 4/1987 | He et al. | 128/660 |
| 4,718,432 | 1/1988 | Kimura | 128/654 |

FOREIGN PATENT DOCUMENTS 2161275  1/1986  United Kingdom ............... 128/653

OTHER PUBLICATIONS

"Experimental Xenon Enhancement with CT Imaging: Cerebral Applications" B. P. Drayer, et al., AJR:134, Jan. 1980 pp. 39-44.

"Local Cerebral Blood Flow by Xenon Enhanced CT" D. Gur, et al. Stroke, vol. 13, No. 6, pp. 750-758, Nov.—Dec. 1982.

"Regional Cerebral Blood Flow Measurements Using Stable Xenon Enhanced Computer Tomography: A Theoretical and Experimental Evaluation" P.R.S. Kishore, et al. J. of Computer Assisted Tomography, vol. 8, No. 4, pp. 619-630, Aug. 1984.

Primary Examiner—Ruth S. Smith
Attorney, Agent, or Firm—Fay, Sharpe, Beall, Fagan, Minnich & McKee

[57] ABSTRACT

A xenon gas system (B) introduces xenon gas into a patient's blood. The xenon gas concentration in the patient's blood is monitored and the characteristics of the patient's blood absorption curve are determined (34). A look-up table array (60) includes a plurality of look-up tables, each look-up table corresponding to one of a plurality of preselected blood absorption curves. A look-up table selection circuit (36) selects the look-up table which most closely corresponds to the projected blood absorption curve. A CT scanner (A) generates a plurality of image representations at preselected intervals after commencement of xenon gas interpolation, which images are stored in an image memory array (44). Xenon gas concentration values from corresponding pixels of each image representation are utilized to address the look-up table corresponding most closely to the patient's blood absorption curve in order to retrieve precalculated partition coefficient, blood flow rate, and confidence values. The retrieved values may be interpolated (80, 82) to compensate for a patient's blood absorption curve falling among a plurality of curves or the measured xenon concentration values falling between the preselected addressable values of the look-up tables. A display (96) displays images indicative of the partition coefficient, the blood flow rate, and the confidence value.

20 Claims, 2 Drawing Sheets

CT BLOOD FLOW MAPPING WITH XENON GAS ENHANCEMENT

BACKGROUND OF THE INVENTION

The present invention relates to the art of medical diagnostics. It finds particular application in conjunction with CT blood flow mapping of the brain and will be described with particular reference thereto. However, it is to be appreciated that the present invention will also find utility in conjunction with other imaging modalities, such as digital x-ray, magnetic resonance, radiation and positron emission, ultrasound, and the like. The present invention is further applicable to imaging other regions of human and veterinary patients, inanimate objects, and other subjects.

In the human brain, blood reaches the tissue in two modes, directly through the arteries and indirectly through other tissue. In normal, healthy brain tissue, blood reaches gray matter at 40 to 140 ml per 100 ml per minute. Gray matter tissue which receives less than 30 ml per 100 ml per minute is not adequately fed for proper functioning and may suffer irrepairable damage. In white matter, cerebral blood flows are typically about one third of those for gray matter, with flows under about 10 ml per 100 ml per minute being considered inadequate. The early detection of brain regions with subnormal blood flows enables corrective action to be taken before the blood tissue is irreversibly damaged.

One of the most common causes of insufficient feeding of the tissue is a blockage in the arterial blood flow. In the past, iodine was utilized as an enhancement agent injected into the blood to facilitate the location of arterial blockages. However, brain tissue membrane blocked the iodine enhancement agent from permeating the tissue. Because the iodine was unable to pass from the blood flow into the tissue, iodine was only able to enhance images of blood in arteries, capillaries, and veins. Iodine was unable to enhance representations of the actual profusion of blood into the tissues.

Unlike iodine, xenon passes from the blood into the brain tissue. Thus, utilizing the xenon as an enhancement agent facilitates the imaging and measurement of blood profusion into the tissue. As the concentration of xenon gas in the patient's blood rises, the concentration of xenon gas in the brain tissue increases, asymptotically approaching an equilibrium concentration. The rate of the exponential xenon gas concentration increase in the tissue is indicative of the blood flow rate. The equilibrium concentration which is asymptotically approached is indicative of a partition coefficient, $\lambda$. The partition coefficient, which is different for different kinds of tissue, is defined as the ratio of the quantity of xenon in each unit volume or voxel of tissue to the quantity of xenon per like volume in blood. For gray matter, the partition coefficient is typically about 0.95 and for white matter is typically about 1.35. Partition coefficients which differ significantly from these values are indicative of sick or dying tissue.

The xenon concentration in the tissue of the ith unit volume or voxel at a time t is described by a formula known as the Kety equation:

$$C(t) = f \int_0^T C_a(w) e^{-K(t-w)} dw, \quad (1)$$

where C is the tissue xenon concentration, $C_a$ is the blood xenon concentration, K is the tissue clearance or build-up rate, and f is the flow rate. The partition coefficient, $\lambda$, is related to the flow rate and the clearance or build-up rate by the equation:

$$f = \lambda K \quad (2),$$

where $\lambda$ is the tissue-blood partition coefficient.

The blood xenon concentration is readily monitorable. The tissue xenon concentration for a tissue in a given voxel can be calculated from the CT number or other data value of a pixel of a CT image corresponding to the given voxel. By taking several CT images at different times, with the blood xenon concentration known for times preceeding each image, one can theoretically solve the Kety equation to determine the partition coefficient and blood flow for the tissue compartment corresponding to each pixel. Typically, three to six images were taken. More particularly, the values or CT numbers from the corresponding pixels of each of the three to six images were iteratively fit to the "best" flow f and partition coefficient which, with the known $C_a(w)$, allowed comparative $C(t)$ to be calculated using any of various conventional curve fitting techniques. Perhaps the most common approximation implemented was the "minimum chi-square" curve fitting criterion which required extended and time consuming calculations. The chi-square curve fitting technique determined a best fit flow, a best fit partition coefficient, and a fit or confidence value indicative of the closeness of the best fit. The curve fitting technique was repeated for each pixel of the images.

It is to be appreciated that chi-square and other curve fitting techniques for fitting three to six data points with a curve, then deriving the slope, the end point which the curve is asymptotically approaching, and the degree of conformity to the curve or best fit was a time consuming operation. When this operation was repeated over 65,000 times to fit the CT numbers of corresponding pixels of a conventional 256×256 image to corresponding curves, the computational time became excessive, even on a high speed computer. To reduce the computation to an acceptable time, the image resolution was commonly reduced from 256×256 pixels to as little as 32×32. However, calculating the flow, partition coefficient, and fit for each of the over 1000 pixels of a 32×32 image still required up to ten minutes.

The present invention contemplates a new and improved technique for more rapidly and more accurately determining the flow, the partition coefficient, and the fit or confidence value from CT or other image data.

SUMMARY OF THE INVENTION

In accordance with the present invention, precalculated flow, partition coefficient, and confidence values are stored for each combination of a plurality of possible sets of image data and arterial blood xenon concentration or absorption curves. When actual image data is collected, the most nearly corresponding precalculated flow, partition, and confidence values are retrieved from memory.

In accordance with a more limited aspect of the present invention, the retrieved flow, partition coefficient, and confidence values are interpolated from the closely corresponding stored memory data.

In accordance with a still more limited aspect of the present invention, a method of determining at least partition coefficient and flow values corresponding to each of a plurality of voxels of a region of interest is provided. After starting to introduce an enhancement agent into the patient, a concentration of the enhancement agent in a preselected patient tissue, e.g. blood, is measured. An absorption curve is projected from the measured enhancement agent concentrations. Also, after starting to introduce the enhancement agent into the patient, a plurality of image representations are generated. Each image representation is defined by a plurality of pixels which correspond to voxels of the region of interest. Each image representation includes a pixel value for each pixel, which pixel value is indicative of enhancement agent concentration in the corresponding voxel. A look-up table array is accessed with at least the projected absorption curve and corresponding pixel values of each of the plurality of image representations generated at different intervals to retrieve the precalculated partition coefficient and flow values.

In accordance with another more limited aspect of the present invention, an apparatus for determining partition coefficients and blood flow rates in a region of interest is provided. An enhancement agent means introduces an enhancement agent into the patient's blood and provides an indication of the enhancement agent concentration within the blood. An absorption curve projecting means projects an absorption curve which is indicative of enhancement agent absorption by the blood from the provided indications of enhancement agent concentration in the blood over time. A look-up table means is preprogrammed with at least precalculated blood flow and partition coefficient values which have been previously calculated in accordance with preselected sampling intervals, pixel values, and preselected absorption curves. The look-up table means is addressed by at least the pixel values and absorption curve values to retrieve at least the corresponding precalculated blood flow and partition coefficient values. An imaging means generates electronic image representations of the region of interest. Each image representation includes a plurality of pixel values, each of which is indicative of enhancement agent concentration in the corresponding voxel of the region of interest. A plurality of image representations are generated, each at a selected sampling interval. A look-up table access means selectively accesses the look-up table means with one or more of the absorption curve, the image pixel values, and the sampling intervals to retrieve at least the most nearly corresponding stored partition coefficient and blood flow values for each of the image pixels.

In accordance with a yet more limited aspect of the present invention, an apparatus is provided for determining partition coefficient, blood flow, and confidence values of each voxel of a region of interest of a patient. A xenon means introduces xenon into the patient's blood and produces a xenon gas concentration signal indicative of xenon concentration in the blood. An absorption curve projecting means projects at least one absorption curve which is indictive of absorption of xenon gas in the blood from the xenon concentration signals. Each of a plurality of look-up tables corresponds to a preselected absorption curve. Each of the look-up tables is preprogrammed with precalculated blood flow, partition coefficient, and confidence values which have been precalculated in accordance with the corresponding absorption curve, pixel values, and preselected sampling intervals. Each look-up table is addressable at least by a xenon gas concentration value to retrieve corresponding precalculated blood flow, partition coefficient, and confidence values. A scanner generates a plurality of image representations. Each image representation is defined by pixels that correspond to preselected voxels of the region of interest and includes a plurality of pixel values that are indicative of radiation altering properties of substances in the corresponding voxels. A reference image memory means stores a reference image representation generated prior to introducing xenon into the patient's blood. A subtraction means subtracts pixel values of the corresponding pixels of the reference image representations and image representations generated at the preselected sampling intervals. In this manner, difference pixel values are created corresponding to each voxel of the region of interest, which difference pixel value is indicative of xenon concentration in the corresponding voxel. A difference image memory means stores a plurality of difference image representations, each corresponding to one of the preselected sampling intervals. The look-up tables are operatively connected with the difference image memory means such that the look-up table corresponding to the projected blood absorption curve is addressed by the corresponding pixel values from each of the plurality of difference images to retrieve the precalculated blood flow, partition coefficient, and confidence values for the corresponding pixel. A partition coefficient memory means stores each retrieved partition coefficient value in a corresponding pixel of a partition coefficient image representation. A blood flow image memory means stores each retrieved blood flow value in a corresponding blood flow image pixel. A confidence image memory means stores each retrieved confidence value in a corresponding confidence image pixel. A display means is operatively connected with the partition coefficient, blood flow, and confidence image memory means for selectively displaying the partition coefficient, blood flow, and confidence images.

A primary advantage of the present invention is that it generates flow, partition coefficient, and confidence images quickly.

Another advantage of the present invention is that it generates flow, partition coefficient, and confidence images with full, detailed resolution. In particular, flow, partition coefficient, and confidence images for $256 \times 256$ pixel images can be done in as little as seven seconds as compared to ten minutes for $32 \times 32$ pixel images of the prior art curve fitting techniques.

Another advantage of the present invention is that it enables interpolated and data improved images of $256 \times 256$ pixel images to be generated in less than four minutes as compared to 646 minutes to calculate $256 \times 256$ pixel images using a chi-square curve fitting technique.

Still further advantages will become apparent to those skilled in the art upon reading and understanding the following detailed description of the preferred embodiment.

BRIEF DESCRIPTION OF THE DRAWINGS

The invention may take form in various components and arrangements of components and in various steps and arrangements of steps. The drawings are only for purposes of explaining and illustrating a preferred embodiment and are not to be construed as limiting the invention.

DETAILED DESCRIPTION OF THE PREFERRED EMBODIMENTS

Figure 1:
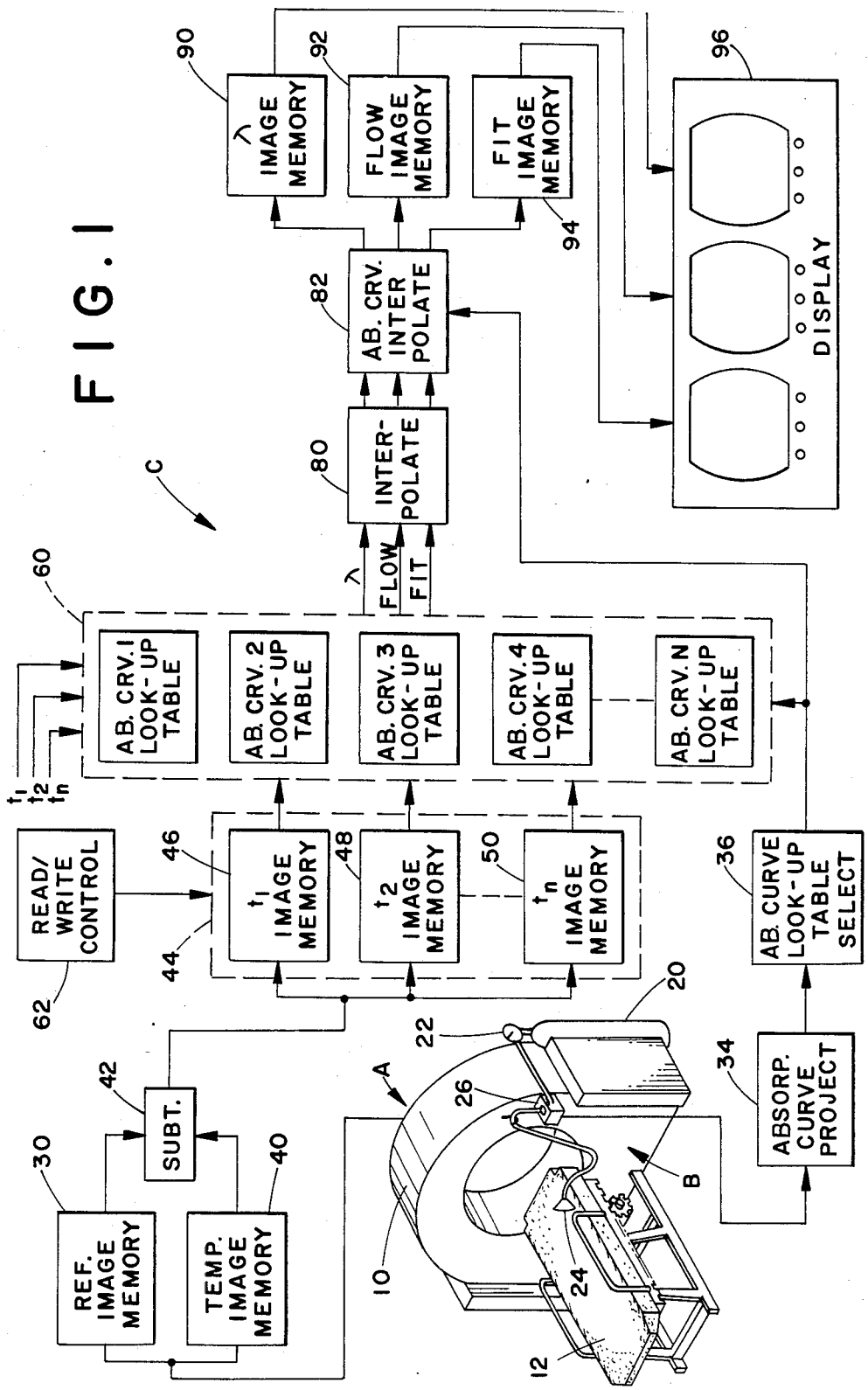
FIG. 1 is a diagrammatic illustration of an imaging apparatus in accordance with the present invention.

With reference to FIG. 1, an imaging means A, such as an axial tomographic scanner, selectively examines a subject and reconstructs image representations depicting properties of each voxel or subregion within an examined region of interest. An enhancement agent system B introduces selected amounts of an enhancement agent into the subject and derives an indication of the concentration of the enhancement agent in at least selected portions of the patient. The enhancement agent is selected such that its concentration or presence in the subject alters the image representations. In the preferred embodiment, the enhancement region is xenon gas whose concentration is reflected in the reconstructed image representations. The resultant image representations are essentially the sum of two images—an image depicting the xenon gas in the voxels of the region of interest and an image of the tissue in the region of interest. A processing means C processes the image data from the scanner A collected with varying concentrations of the enhancement agent and processes the enhancement agent concentrations from the enhancement agent system B to derive images representing the partition coefficient or permeability, blood or other fluid flow rates, and a confidence value or degree of fit.

The imaging means A may be a CT scanner, a digital x-ray scanner, a magnetic resonance imager, or other diagnostic scanning device which generates data which can be reconstructed into a representation of an image of a region of interest. In the CT scanner embodiment, the scanner includes a gantry 10 which houses a rotating x-ray source and radiation detectors. Images from a CT scanner are indicative of x-ray absorption/transmission properties of tissue in each voxel of a planar region of interest or slice. In a magnetic resonance scanner, the gantry 10 houses appropriate electromagnetic coils and antennae. A patient supporting couch 12 selectively indexes a patient through the gantry such that one or more planar slices are selectively imageable.

The enhancement agent supply system B includes a source 20 of the enhancement agent, such as a tank of xenon gas. A flow or pressure regulator 22 controls the supply rate of the xenon gas to a breathing mask 24 or other means for introducing the enhancement agent into the patient. An enhancement agent concentration means 26 determines concentrations of the enhancement agent within the patient. It is well known that there is a linear relationship between the xenon concentration in exhaled breath at the end of an exhalation cycle and the concentration of xenon gas in a patient's blood. In the preferred embodiment, the enhancement agent concentration means 26 measures the concentration of xenon gas at the end of a respiratory cycle and provides an output signal indicative thereof.

Figure 2:
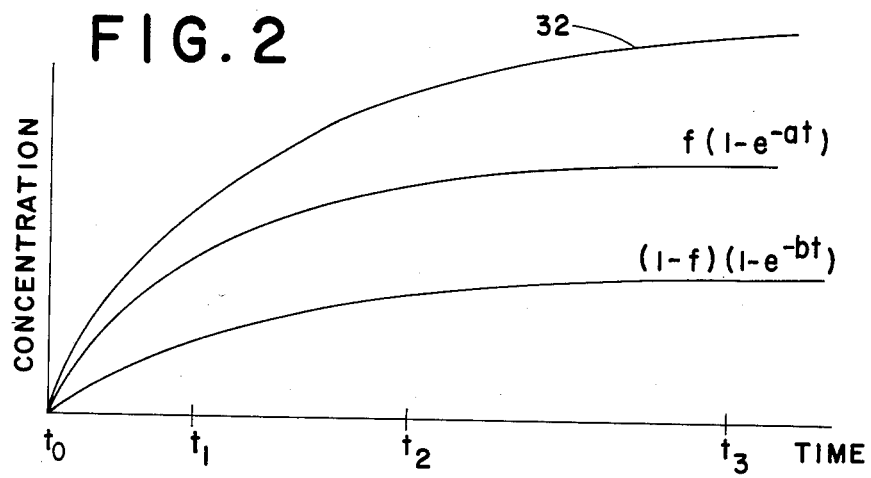
FIG. 2 illustrates a technique for determining a patient's blood absorption curve.

Before the xenon gas or other enhancement agent is introduced to the patient, a reference scan is conducted to generate an image representation depicting the imaged region without the enhancement agent. The reference image is stored in a reference image memory 30. Upon completion of the reference image at a time t, the enhancement agent system B starts supplying xenon gas to the patient. For example, xenon may be substituted for 30% of the gases breathed by the patient. At the end of each respiratory cycle, generally every few seconds, the breath analyzer means 26 determines the concentration of xenon gas in the patient's blood. The increase in xenon concentration in the blood with time normally increases exponentially as illustrated in curve 32 of FIG. 2.

Generally, the data acquisition period lasts for several minutes, e.g. five to seven minutes. During this time, some 50 or more xenon concentration readings are commonly made by the breath analyzer means 26. A curve fitting means 34 utilizes known curve fitting techniques to project an absorption curve which is indicative of the absorption of xenon in the patient's blood. That is, the curve fitting means generates equations which describe the parameters of a curve 32 that most closely fits the discrete data points from the breath analyzer 26. Various conventional curve fitting techniques may be implemented. In a preferred embodiment, the curve fitting technique implements a double exponential fit. That is, from the breath analyzer data points, two exponential curves are determined, which two curves sum to produce a curve which follows the actual blood flow concentration. The double exponential fit technique requires the determination of three variables: a scaler multiplier f and two exponential values, a, b. That is:

$$f(1-e^{-at})+(1-f)(1-e^{-bt}) \tag{3}$$

Optionally, other curve fitting techniques may be implemented. However, more precise curve fitting techniques, such as those that describe the curve in terms of three or more parameters are preferred. The values of the three or other number of parameters which describe the absorption curve are used to address a blood curve selection means 36 such as a three dimensional look-up table.

The three dimensional blood curve selection look-up table 36 is addressable only by preselected values of the three parameters. Normally, each of the three calculated parameter values falls between two preselected address values. In one embodiment, the preselected address value that is closest to the calculated value is used as the address. In another embodiment, each of the eight combinations of adjoining preselected address values are used to retrieve eight blood curves, which may all be the same.

As the xenon concentration in the patient's blood is building, a plurality of images of the planar region are generated at preselected sampling intervals or times. As each image is reconstructed, it is stored in a temporary memory 40. A subtraction means 42 subtracts the xenon image from the reference image stored in the reference image memory means 30 to produce a difference or xenon concentration image representative only of xenon concentration. A difference image memory 44 stores a plurality of difference images, each corresponding to a different sampling interval.

A first xenon enhanced scan is conducted a first preselected sampling interval t1 after the patient commences breathing xenon gas. This first produces a first image from which the reference image is subtracted to produce a first difference image that is stored in a first difference image memory 46. At a second preselected sampling interval or time after the patient starts breathing the xenon gas, t2, a second scan generates a second image from which the reference image is subtracted to produce a second difference image that is stored in a second image memory 48. In the preferred embodiment, a third difference image memory 50 stores a third difference image which is generated from a scan at a third sampling interval t3. Fourth and additional image memories are contemplated as may be appropriate to the degree of precision required. In the preferred embodiment, the first sampling interval is 1½ minutes after $t_o$, the second sampling interval t2 is 3 minutes after $t_o$, and the third sampling interval t3 is 5 minutes after $t_o$. Optionally, a fourth image may be taken at a fourth sampling interval of 7 minutes.

Each difference image is defined by an array of pixels which each correspond to a voxel of the region of interest. Corresponding pixels of each difference image stored are those that depict the same voxel but at a different sampling interval or time. The concentration of xenon in the corresponding pixels can be expected to increase logarithmically with time, analogous to curve 32. The CT number or other value stored for the corresponding pixel of each difference memories 46, 48, 50 is proportional to the concentration of xenon gas in the corresponding voxel at the sampling interval t1, t2, t3, etc. If a voxel is totally within an unblocked artery, the concentration would be expected to follow the blood-xenon absorption curve 32 exactly. If the pixel is in tissue, the increase in xenon concentration might be expected to somewhat less. The exact concentration is determined by the Kety equation (1) discussed above.

A look-up table means 60 is preprogrammed with a blood flow value and partition coefficient stored in each memory element. Each memory element is addressed by a corresponding combination of preselected addressing absorption curves, pixel values, and sampling times. By addressing the look-up table means with the preselected addressing absorption curve, pixel values, and sampling times that are closest to the absorption curve projected by the curve projecting means 34, the corresponding pixel values of difference memory means 44, and the actual sampling interval, corresponding blood flow, and partition coefficient values are retrieved. Various techniques may be utilized to calculate the correspondence of the flow values and partition coefficients stored in the look-up table with the addressing values.

In the preferred method for loading the look-up table, partition coefficients, blood flow rates, and absorption curves are selected which span the range normally encountered in human patients. The number of partition coefficients, blood flow rates, and absorption curves selected determines the precision with which the final answer is reached but increases the size of the look up table and the complexity of the calculations to fill it. For a given blood flow rate, partition coefficient and absorption curve, xenon concentration curves are calculated from the Kety equation. The calculated xenon concentration curves give the exact concentration at each of the preselected sampling intervals or times t1, t2, and t3, i.e. the concentration or pixel values which address each stored blood flow value and partition coefficient.

Because all possible concentrations which might be measured at t1, t2, and t3, will not fall exactly on a theoretically calculated xenon concentration curve, many of the look-up table entries will remain unfilled. To fill these remaining look-up table entries, the CT number values theoretically predicted at each sampling time are varied randomly a small amount. These stochastic variations generate additional look-up table entries with varying likelihoods. The most likely flow and lambda values are then used to fill this matrix value and the degree of likelihood or "confidence" value is also stored.

It is to be appreciated that the reliability of flow and partition coefficient values generated by large deviations in observed CT absorption are less reliable than flow and lambda data which corresponds precisely to one of the theoretical curves. To advise the viewer of the degree of fit to the theoretical curves, the confidence value is stored in the corresponding memory element along with the stored partition coefficient and flow rate.

Looking now to a preferred organization of the look-up table means 60, a plurality of look-up tables are provided, each look-up table corresponding to one of a plurality of preselected blood curves, i.e. $C_a(w)$ in Equation (1), and xenon enhanced measurement times t1, t2, t3. The look-up table selection means 36 selects at least the look-up table which was precalculated in accordance with the absorption curve which is most like the patient's blood curve $C_a(w)$ and the selected sampling times t1, t2, t3. Each of the look-up tables is an n dimensional look-up table, where n is the number of difference images generated and stored in the image memory means 44 during a single examination.

Figure 3:
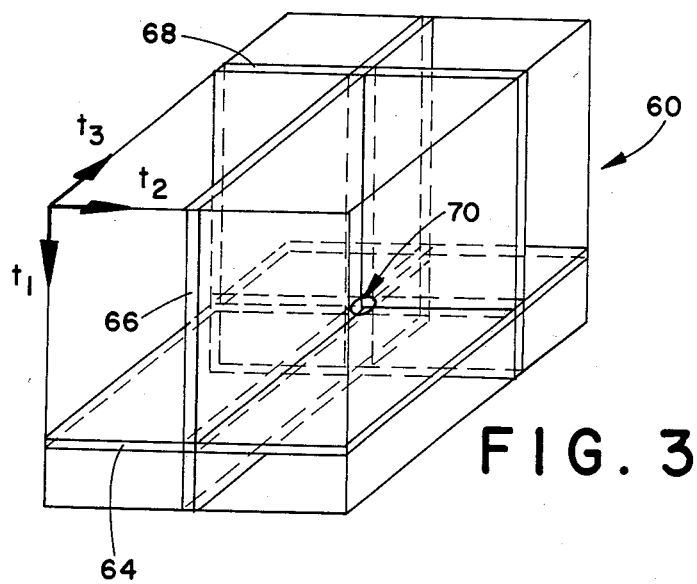
FIG. 3 illustrates a three dimensional data organization for the look-up tables of FIG. 1; and, FIG. 4 illustrates a data interpolation technique for interpolating data from the look-up tables of FIG. 1.

For simplicity of illustration, the organization of each individual look-up table is described in conjunction with three images per study, i.e. a three dimensional look-up table. As illustrated in FIG. 3, t1, t2, and t3 are the coordinates of a three dimensional look-up table. The magnitude of the preselected addressing xenon concentrations, CT numbers, or pixel values along each axis function as the look-up table. It is to be appreciated that additional sampling intervals e.g., t4, may also be accomodated. Further, additional look-up tables may be provided for different sampling intervals or numbers of sampling intervals.

Figure 4:
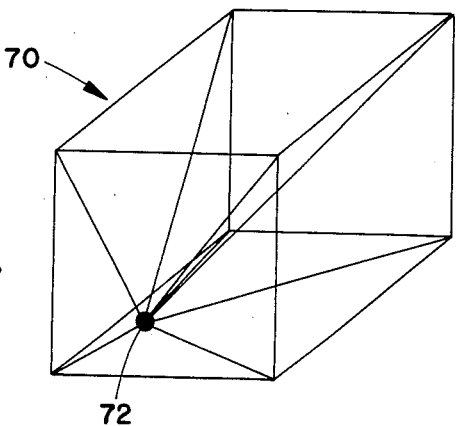

During a patient scan, a read control means 62 causes the pixel value or CT number corresponding to the same pixel in each image to be read from the difference images taken at sampling intervals t1, t2, and t3. As illustrated in FIG. 3, the pixel value from the pixel of the t1 image which normally falls between two precalculated xenon concentration values defines a planar region of possible solutions 64. The thickness of the planar region is determined by the distance between adjacent precalculated addressing xenon concentrations or pixel values. The data value from the t2 image similarly defines a planar region 66 and the data value taken from the t3 image determines a planar region of possible solutions 68. With reference to FIGS. 3 and 4, the intersection of these three planar regions defines a volume or cube 70 within which point 72 defined by the three actual pixel values falls. The precalculated blood flow, partition coefficient and confidence values are stored in memory elements corresponding to each corner of the volume. The partition coefficient, flow value, and confidence values at the closest corner are retrieved and read out of the look-up tables 60.

For greater accuracy, the partition coefficient, flow rate, and fit may be interpolated from values stored in the eight memory elements at the corners of the volume 70 by interpolating means 80. In a preferred embodiment, the distance between the point 72 and each corner is calculated. The partition coefficient, flow rate, confidence value from the memory element at each corner is weighted in inverse proportion to the calculated distance. The weighted retrieved values are summed.

As indicated above, the theoretical blood-xenon absorption curve projected by absorption curve calculating means 34 in many instances will not describe one of the preselected addressing absorption curves precisely. Rather, the value may tend to fall between two or more of the precalculated absorption curves. Because the absorption curve is described by three variables in the preferred embodiment, variables may address a point within a volume defined by eight corners as discussed above in conjunction with FIG. 4. In the preferred embodiment, the look-up tables corresponding to each of the eight corners absorption curves are also addressed by each pixel value to generate eight sets of partition coefficients, flow rates, and fit values. Each of the eight sets is interpolated by the first interpolating means 80. A second interpolating means 82 performs a weighted averaging of eight partition coefficients, flow rates, and confidence values from the first interpolating means. The weighting is again in inverse proportion to the distance between 72 and the corners. It is to be appreciated that the processing may be simplified when several corners of absorption curve look-up table 36 define the same absorption curve.

The sampling times t1, t2, and t3 may also be varied. To vary the sampling times, additional sets of look-up tables are provided for each additional sampling time combination. A third interpolating means may be provided to adjust for differences between the actual sampling time and the look-up tables actually provided. The interpolated partition coefficient values corresponding each pixel are stored in corresponding pixels of a partition coefficient image memory means 90. Analogously, the blood flow rates retrieved for each pixel are stored in a flow image memory means 92 and the retrieved fit or confidence values are stored in a fit or confidence image memory means 94. A display means 96 displays partition coefficient, flow rate, and fit or confidence images.

The look-up tables 60, as well as the absorption curve select look-up table 36, are all described as three dimensional look-up tables. Optionally, other dimensions may be provided. Single dimensional look-up tables could be utilized but may produce suspect partition coefficients, flow values, and confidence value images. Dimensions higher than those can produce greater accuracy and higher confidence values.

The invention has been described with reference to the preferred embodiment. Obviously, modifications and alterations will occur to others upon reading and understanding the preceding specification. It is intended that the invention include all such alterations and modifications insofar as they come within the scope of the appended claims or the equivalents thereof.

Having thus described the preferred embodiment, the invention is now claimed to be:

1. An apparatus for determining partition coefficients and blood flow rates in a tissue region of interest of a subject, the apparatus comprising:

an enhancement agent means for introducing an enhancement agent into a patient's blood;

a means for providing an indication of a concentration of the enhancement agent within the blood over time;

an absorption curve projecting means for projecting an absorption curve designation indicative of one of a plurality of preselected absorption curves representing enhancement agent absorption by the blood from the provided indications of the enhancement agent concentration in the blood over time;

a look-up table means preprogrammed with blood flow and partition coefficient values which have a previously calculated relationship to preselected sampling intervals, image pixel values, and blood enhancement agent absorption curve designations, the look-up table means being addressable at least by the image pixel values and the absorption curve designations to retrieve the corresponding precalculated blood flow and partition coefficient values;

an imaging means for generating electronic image representations of at least the tissue region of interest, each image representation including a plurality of image pixel values, each pixel value being indicative of enhancement agent concentration in a corresponding subregion of the tissue region of interest;

an image representation storing means for storing a plurality of image representations of the selected region of interest, the stored image representations being generated at selected sampling intervals; and, a look-up table access means for selectively accessing the look-up table means with at least the projected absorption curve designation and the image pixel values to retrieve the corresponding preprogrammed partition coefficient and blood flow values.

2. The apparatus as set forth in claim 1 further including a partition coefficient image memory means for storing a partition coefficient image representation in which the retrieved partition coefficient values from the look-up table means are stored as pixel values for pixels corresponding to the same subregion as the stored image representation pixels.

3. The apparatus as set forth in claim 2 further including a blood flow image memory means for storing a blood flow image representation in which the retrieved blood flow values from the look-up table means are stored as pixel values for blood flow image pixels corresponding to the same subregions as the stored image representation pixels.

4. The apparatus as set forth in claim 3 further including a display means for displaying man-readable images, the display means being operatively connected with the partition coefficient and flow memory means, to display the partition coefficient and blood rate image representations.

5. The apparatus as set forth in claim 1 wherein the imaging means includes an x-ray examination apparatus.

6. The apparatus as set forth in claim 5 wherein the x-ray examination apparatus includes a CT scanner.

7. The apparatus as set forth in claim 1 wherein the look-up table means includes a plurality of look-up tables each corresponding to one of the plurality of preselected absorption curves and wherein the look-up table accessing means includes a look-up table selecting means for selecting at least the look-up table which corresponds most closely to the projected absorption curve designation.

8. The apparatus as set forth in claim 7 wherein the absorption curve projecting means defines the projected absorption curve in terms of a plurality of curve designation defining parameters and wherein the look-up table selecting means includes a multidimensional look-up table which is addressed by the plurality of curve defining parameters to retrieve the designation of at least the most nearly corresponding preselected absorption curve.

9. The apparatus as set forth in claim 7 further including:
- a reference image storage means for storing a reference image representation of the region of interest generated without the enhancement agent in the blood; and,
- a subtraction means for subtracting the reference image representation from the image representation generated at each of the selected sampling intervals to create difference image representations each having difference image pixel values that are indicative of enhancement agent concentration in the corresponding subregion of the region of interest at the corresponding selected sampling interval, the look-up tables being addressed by the corresponding difference pixels values.

10. The apparatus as set forth in claim 1 further including an interpolating means for interpolating retrieved partition coefficient and blood flow values.

11. An apparatus for determining and displaying partition coefficient, blood flow, and confidence values for each of a plurality of voxels of a tissue region of interest of a patient, the apparatus comprising:
- a xenon means for introducing xenon into blood of the patient and for producing a xenon concentration signal indicative of the xenon concentration in the blood;
- an absorption curve projecting means for projecting at least one absorption curve indicative of blood absorption over time of xenon from the xenon concentration signals;
- a plurality of look-up tables, each look-up table corresponding to a preselected absorption curve, each look-up table being preprogrammed with preselected blood flow, partition coefficient, and confidence values which have been preselected to correspond with preselected absorption curves and preselected tissue xenon concentration values and preselected sampling intervals, each look-up table being addressable at least by a tissue xenon gas concentration value to retrieve corresponding preselected blood flow, partition coefficient, and confidence values;
- a scanner for generating image representations of the tissue region of interest at least at the preselected sampling intervals, each image representation being defined by pixels that correspond to the voxels of the tissue region of interest including a plurality of pixel values that are indicative of radiation altering properties of substances in the corresponding voxels;
- a reference image memory means for storing a reference image representation generated prior to commencement of introducing the xenon into the patient's blood;
- a subtraction means for subtracting pixel values of the corresponding pixels of the reference image representation and image representations generated at said preselected sampling intervals to produce difference pixel values indicative of xenon concentration in the corresponding voxel;
- a difference image memory means for storing a plurality of difference image representations each difference image representation corresponding to one of the preselected sampling intervals, the difference image memory means being operatively connected with the look-up tables for addressing the look-up table corresponding to the projected absorption curve with corresponding pixel values from each of the plurality of difference images to retrieve the preprogrammed blood flow, partition coefficient, and confidence values;
- a partition coefficient memory means for storing each retrieved partition coefficient value in a corresponding partition coefficient image pixel;
- a blood flow image memory means for storing each retrieved blood flow value in a corresponding blood flow image pixel;
- a confidence image memory means for storing each retrieved confidence value in a corresponding confidence image pixel; and
- a display means operatively connected with the partition coefficient, blood flow, and confidence image memory means for selectively displaying the partition coefficient, blood flow, and confidence images.

12. A method of determining at least a selected one of partition coefficient and flow values of each of a plurality of voxels of a region of interest of a subject, the method comprising:
- at a commencement time, start introducing an enhancement agent into the subject;
- repeatedly measuring a concentration of the enhancement agent in a fluid of the subject;
- projecting an absorption curve from the measured enhancement agent concentrations;
- selecting at least one of a precalculated family of preselected absorption curves which corresponds most closely with the projected absorption curve;
- generating a plurality of image representations each at a selected sampling interval subsequent to the commencement time, each image representation being defined by a plurality of pixels corresponding to voxels of the region of interest and including a pixel value for each pixel which pixel value is indicative of an enhancement agent concentration in the corresponding voxel;
- accessing a look-up table array with at least the selected curve of the absorption curve family and corresponding pixel values of image representations generated at different intervals to retrieve the selected one of precalculated partition coefficient and flow values therefrom.

13. The method as set forth in claim 12 further including prior to the commencement time:
- (i) calculating corresponding partition coefficient and flow rate values and (ii) absorption curves, sampling intervals, and pixel values in accordance with a Kety equation;
- storing the precalculated partition coefficient and flow values in the look-up table array; and,
- defining at least the precalculated absorption curves and pixel values as addresses to index the look-up table array.

14. The method as set forth in claim 12 wherein the look-up table array includes a plurality of look-up tables, each look-up table corresponding to a preselected absorption curve and being addressable by pixel values generated at preselected sampling intervals, and further including:
   conducting the image representation generating step at the preselected sampling intervals; and,
   selecting the look-up table which most closely corresponds to the projected absorption curve.

15. The method as set forth in claim 14 further including interpolating the retrieved partition coefficient and flow values from a plurality of look-up tables which most closely correspond to the projected absorption curve.

16. The method as set forth in claim 12 wherein the look-up table array is addressable by preselected pixel values and further including interpolating partition coefficient and blood flow values which are retrieved by addressing the look up table array with preselected pixel values that are close to the pixel values from the generated image representations.

17. The method as set forth in claim 12 further including the step of displaying man-readable images defined by pixels that correspond to the voxels of the region, a first image repesenting the partition coefficients and a second image representing flow values.

18. The method as set forth in claim 12 further including imaging the patient prior to the commencement time to create a reference image and subtracting the reference image from each subsequent image such that the stored pixel values are indicative of a difference image attributable substantially solely to the presence of the enhancement agent in each voxel.

19. The method as set forth in claim 12 wherein the enhancement agent is xenon.

20. The method as set forth in claim 12 wherein the image representation generating step includes radiographically examining the patient.

* * * * *